(12) United States Patent
Singh-Verma

(10) Patent No.: US 6,361,804 B2
(45) Date of Patent: *Mar. 26, 2002

(54) **COSMETIC FORMULATIONS CONTAINING EXTRACTS FROM *PHYLLANTHUS EMBLICA* AND *CENTELLA ASIATICA* AND/OR *BACOPA MONNIERI***

(76) Inventor: Shyam B. Singh-Verma, Nussbaumallee 13, 50169 Kerpen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/820,873

(22) Filed: Mar. 30, 2001

Related U.S. Application Data

(63) Continuation of application No. 09/331,791, filed as application No. PCT/EP97/07113 on Dec. 18, 1997, now Pat. No. 6,261,625.

(30) Foreign Application Priority Data

Dec. 28, 1996 (DE) .......................... 196 54 635

(51) Int. Cl.$^7$ .......................... A61K 35/78; A61K 7/00
(52) U.S. Cl. .................. 424/725; 424/401; 424/744; 424/773; 424/774; 424/777; 424/779
(58) Field of Search .................. 424/725, 744, 424/773, 774, 777, 779, 401

(56) References Cited

U.S. PATENT DOCUMENTS 4,459,285 A 7/1984 Grollier et al.
5,427,776 A 6/1995 Isnard

FOREIGN PATENT DOCUMENTS

| CA | 1334578 | 2/1995 |
| EP | 277455 | 8/1988 |
| EP | 0345571 A | 12/1989 |
| FR | 1433383 A | 6/1966 |
| GB | 2274058 A | 7/1994 |

OTHER PUBLICATIONS

J.F. Morton, "The Emblic (*Phyllantus emblica* L:)", Economic Botany, vol. 14, XP002063499, pp. 119–128, dated 1960.
F. D'Amelio: "Gotu Kola", Cosmetics & Toiletries, vol. 102, No. 6, pp. 49–50, XP002063500, dated 1987.
Patent Abstracts of Japan, vol. 015, No. 206 (C–0835), May 1991, JP 03 058939A, (Toreede Unindo KK), Mar. 1991.
Doris E. Billiek et al. "Fette und Ole Fettderivate Folgeprodukte" dated Oct. 1989 (w/English translation).
Hagers Handbuch der Pharmazeutischen Praxis, "Centella", dated 1972 (w/English translation).

*Primary Examiner*—Francisco Prats
*Assistant Examiner*—Susan D. Coe
(74) *Attorney, Agent, or Firm*—Banner & Witcoff, Ltd.

(57) ABSTRACT

The present invention relates to cosmetic formulations for topical application containing extracts from *Phyllanthus emblica* and *Centella asiatica* and/or *Bacopa monnieri*, and the use of such formulations for the care of the human skin. In particular, the present invention relates to cosmetic formulations for topical application containing extracts from *Phyllanthus emblica* and *Centella asiatica* and/or *Bacopa monnieri* in addition to per se known adjuvants and expedients.

7 Claims, No Drawings

COSMETIC FORMULATIONS CONTAINING EXTRACTS FROM *PHYLLANTHUS EMBLICA* AND *CENTELLA ASIATICA* AND/OR *BACOPA MONNIERI*

This application is a continuation of U.S. patent application Ser. No. 09/331,791, filed Jul. 27, 1999, now U.S. Pat. No. 6,261,625, issued Jul. 17, 2001, which is a 371 of PCT/EP97/07113, filed Dec. 18, 1997.

The present invention relates to cosmetic formulations for topical application containing extracts from *Phyllanthus emblica* and *Centella asiatica* and/or *Bacopa monnieri*, and the use of such formulations for the care of the human skin.

According to the German Lebensmittel- und Bedarfsgegenstandsgesetz (LMBG; food and utility item act), 4th Section, of Aug. 15, 1974, the EC Directive (76/768/EEC) of Sep. 27, 1976, and the German Kosmetik-Verordnung (cosmetics regulation) of Jun. 26, 1985, cosmetic agents are materials or formulations made of substances which are designated for topical application on humans or in their oral cavities for cleaning, care and protection, inter alia. When this definition was established, the idea of consumer protection was given priority.

Especially dermatologists had long been of the opinion that few substances besides water could pass through the barrier layer of the skin, and thus cosmetic agents had no effect, or should not have any. In the meantime, it could be proven that a wide variety of substances can penetrate even intact and healthy skin depending on their molecular weight, molecular structure and size. If special carrier substances, especially emulsifiers, are additionally employed, the number of such substances can be increased many times over.

From cosmetic agents, the consumer also expects specific effects, such as the prevention of premature skin aging, the avoiding or delaying of wrinkle formation, or effective protection against drying of the skin. It is taken for granted that the ingredients employed are free of deleterious actions.

This expectation by the consumer led to the development of so-called "active cosmetics", the active ingredients employed being not allowed to have systemic effects, however. In particular, vitamins, minerals and trace elements or animal proteins have been used.

In contrast, in the field of medicinal plants, there are great opportunities of achieving the above mentioned effects without appreciable risks to health, since tolerance thereof is sufficiently proven from the tradition of folk medicine in all important cultures. In particular, the activity of phytopharmaceuticals is based on that fact; in many cases, the active substances from plants have also been used as pure substances. The activity of plant extracts is often lower than that of pure substances. There are also cases, however, where the components of an extract display their activity only as a whole. For chronic diseases, phytopharmaceuticals offer a true alternative to allopathic medicaments, having fewer risks to health.

The 5th edition (1995) of the "International Cosmetic Ingredient Dictionary", edited by the American industrial association CTFA, lists about 300 plants which are added as active ingredients to cosmetic agents in various formulations. A less extensive list, "Einsatz von pflanzlichen Wirkstoffen und Extrakten in der Hautpflege", has been published by D. Bilek, S. B. Singh-Verma and P. Bernhardt (1989), S ÖFW 115, annual volume No. 19, p. 331–338.

EP 0 345 571 B1 relates to a plant extract composition to be used in cosmetics, which especially comprises a tincture prepared from air-dried fruits of the amla plant (emblic; *Phyllanthus emblica*). The amla fruit (myrobalane) is an Indian medicinal plant; its medical properties have been extensively described in "Economic Botany" 14/1960, p. 119–128. The tincture from amla fruit mainly contains, in high concentrations, anti-inflammatory tannins, mucic acid, various fruit sugars and a number of free amino acids as well as naturally stabilized vitamin C. As could be proven in extensive application tests with skin and hair care products containing amla tincture, this mixture of substances is highly suitable as a cosmetic agent.

As another medicinal plant of importance to the cosmetics industry, there is to be mentioned Gotu Kola (Brahmi). This designation comprises two species in varying proportions, namely "*Centella asiatica*" and "*Bacopa monnieri*", which are used singly or in combination, depending on the intended use. As the active ingredients of a primary tincture prepared according to HRB I, there are mentioned the alcaloid hydrocotyline, the triterpenic acids (asiatic acid, madecassic acid, madasiatic acid) and the triterpene saponin asiaticoside (Haager's Handbuch der Drogenkunde). The oral application of an infusion of the medicinal plant is said to have blood-purifying, tonicising and diuretic properties. When applied topically, the extracts and tinctures have antiphlogistic, antibacterial and wound-healing effects which are said to be attributable to an influence on the formation of collagen fibers which occurs in the fibroblasts, i.e., an increased formation of collagen while scarring is retarded.

From "Hager's Handbuch der Pharmazeutischen Praxis", Springer Verlag, 1972, 3rd volume, p. 792–793, it is known that the active substance madecassoid has an anti-inflammatory effect, while asiaticoside, which stimulates mitoses, promotes the healing of premitis and wounds.

In juvenile adults, the renewal of the horny layer is known to take place in a cycle of about three weeks. With increasing age, this rate of proliferation slows down significantly, for example, in 50-year-old and older people. This means that the skin is renewed in a five- or even six-week cycle rather than in a three-week one, and in consequence, it becomes thinner and also drier under the influence of deleterious environmental conditions. The result thereof is the formation of visible wrinkles in the face and body areas.

Thus, it has been the object of the present invention to provide cosmetic formulations for topical application for the care of the human skin, especially for accelerating the natural regeneration of the skin.

In a first embodiment of the invention, the above object is achieved by cosmetic formulations for topical application containing extracts from *Phyllanthus emblica* and *Centella asiatica* and/or *Bacopa monnieri* in addition to per se known adjuvants and expedients.

Surprisingly, it has been found that a combination of the two extracts, when used as active ingredients in skin and body care preparations, has a special cosmetic and care-providing property which results in an acceleration of the natural regeneration of the skin.

In addition to the two extracts mentioned above, in preferred embodiments, the invention provides the use of additional *Aloe barbadensis* and *Hibiscus sabdariffa* as emollients having moisturizing or moisture-binding and skin-smoothing properties.

It is considered in the invention that the components of the extracts are available as active substances which quickly act on the surface of the skin. It is particularly important that the components be extracted from the plant parts of the amla plant or the Gotu Kola as gently and completely as possible. The extraction method to be employed essentially depends on the kind of care product to be prepared for which the respective extract is to be used. The components of the amla plant are known to have an astringent and degreasing effect and, in long-term applications, a positive influence and clearly regulating effect on the activity of the sebaceous glands. In face and skin care preparations for greasy or problematic skin, a clear cosmetic effect results at higher concentrations of use. By the application of a corresponding extract, the skin is already tightened and gets a smooth and supple appearance without comedones or other skin impurities. A low dosage is known to result in an excellent tonicising and regenerating effect for dry and mixed skin. Ethanolic extracts, especially ethanolic extracts from fruits, are of particular importance as skin care products for greasy, but also for dry and mixed skin (in low dosage).

"Extract" within the meaning of the present invention comprises an extract from the plant parts mentioned as obtained by means of a solvent, optionally under pressure and/or heat. The quality and quantity of the composition of active substances may slightly vary depending on the extractant and extraction method employed.

Of particular importance are extracts from fruits, which may be processed both fresh and in a dried form (amla). Similarly, the extract or the oily extract of *Centella asiatica* may also be obtained from stalks, flowers, leaves or roots. In a preferred embodiment of the present invention, the formulations contain from 0.1 to 40% by weight of the extracts, especially from 1 to 20% by weight of the extracts, of *Phyllanthus emblica* and from 1 to 20% by weight of *Centella asiatica* and/or *Bacopa monnieri*, the stated weight proportion for the combination of *Centella asiatica* and *Bacopa monnieri* referring to the total amount of the two components. If too low a concentration of use is selected, the desired effect will not be achieved. However, if the amounts of extracts are adjusted too high, an economical exploitation is not possible. In addition, considerable galenic problems result in the processing of extracts in the cosmetic formulations.

In addition to the extracts mentioned, the cosmetic formulations optionally contain per se known adjuvants and expedients, such as those known, for example, from Sucker, Fuchs and Speiser, "Pharmazeutische Technologie" (1978); Schrader, "Grundlage und Rezepturen der Kosmetika" (1989); and Nowak, "Die kosmetischen Präparate", 2nd ed. (1975). There may be mentioned, in particular, vegetable oils, alcohols, emulsifiers, antioxidants, thickeners, UV absorbers, vitamins, minerals, trace elements and/or perfume. For example, a particularly preferred formulation is a fluid which consists of natural active substances and the mentioned plant extracts only. The latter stimulate blood circulation and promote the regeneration of the skin. Natural oils adjust the lipid and moisture balance of the skin and confer elasticity and resilience to it. Vitamins stimulate the cellular activity and protect from environmental influences. Preferably, the fluid is free from colorants and preservatives, quickly penetrates into the skin and does not cause a greasy feel. Further formulations are oil-in-water (o/w) emulsions, for example, moisture fluids or night creams.

Another embodiment of the present invention relates to the use of formulations as defined above for the care of the human skin, especially for accelerating the natural regeneration of the skin.

Since the performance of animal studies for the development of cosmetics is banned under German law, it was not possible to directly prove the epidermic proliferation. Therefore, application tests were performed in several steps under strictly controlled conditions in order to prove a synergistic effect of a combination of extracts from *Phyllanthus emblica* and *Centella asiatica* and/or *Bacopa monnieri*.

Therefore, from the full drug, i.e., air-dried fruits of *Phyllanthus emblica* (amla), primary tinctures (extracts) were prepared according to HRB I (extractant: 70% ethanol and 30% demineralized water) and used as active ingredients for cosmetic agents (amla tincture).

EXAMPLES

Comparative Example 1

In strictly controlled groups of 15 subjects, the following excipients were compared:

shaking emulsion:
consisting of natural triglycerids, such as safflower oil, oil of sweet almonds, apricot kernel and sesame oil, in a total amount of 79% by weight; 8% by weight of ethanol; 10% by weight of care substances and vitamins, such as *Aloe barbadensis, Hibiscus sabdariffa*, algal gel, marshmallow and chamomile flower extracts, vitamin A palmitate, vitamin E acetate; 1% by weight of adjuvants, such as silk proteins, lecithin, antioxidants, perfume; as well as 2% by weight of amla tincture.

oil-in water emulsions on the basis of non-ionogenic emulsifiers:
1.) lipid phase, consisting of the emulsifier triceteareth-40 phosphate in an amount of 5% by weight, a lipid component including natural oils and antioxidants in an amount of 7.5% by weight, a UV filter in an amount of 1.5% by weight;
water phase in an amount of 74% by weight of water including preservatives and thickeners;
care substances and vitamins in an amount of 10% by weight; such as allantoin, propylene glycol, vitamin A palmitate, vitamin E acetate, *Aloe barbadensis, Hibiscus sabdariffa* and perfume;
as well as 2% by weight of amla tincture.
2.) lipid phase, consisting of a mixture of the emulsifiers glyceryl stearate and PEG-100 stearate in an amount of 5% by weight, beeswax, Lanette N and isopropyl palmitate in a total amount of 7% by weight, a lipid component including natural oils and antioxidants in an amount of 25% by weight;
water phase in an amount of 50% by weight;
care substances and vitamins in an amount of 11% by weight; such as butylene glycol, allantoin, algal extraxt, D-panthenol, vitamin A palmitate, vitamin E acetate and perfume;
as well as amla tincture in an amount of 2% by weight.

The active substance "amla tincture" was incorporated in the two expedient systems, i.e., shaking emulsion and the two o/w creams. For each expedient system, two laboratory scale preparations were prepared with and without amla tincture. The shaking emulsions were filled in 30 ml glass bottles, and the creams in 50 ml collapsible tubes, and provided with different lot numbers.

Three groups of five subjects each were formed to test all three expedient systems in one experimental run. The subjects were predominantly females aged between 40 and 58 years. Each group of subjects received the corresponding product patterns with and without the addition of active ingredients. The formulation containing the active ingredient and the corresponding placebos were each applied to one half of the face in the morning and in the evening after cleaning the face as usual. The duration of the application experiment was six weeks. Twice per week, the smoothness and elasticity of the skin as a measure of the regeneration of the skin as well as the subjective feeling by the subjects themselves, such as skin tension, feeling of dryness and the like, were evaluated.

After three weeks of application, it was found that the shaking emulsion as an excipient system yielded a clearly better result as compared with the two o/w creams, not only with respect to the skin smoothness and elasticity evaluation criteria, but also in the subjective evaluation by the users. In addition, in contrast to commercially available creams, the quick penetration of the natural oils into the skin without inconvenient sticky effects as well as the convenience in the application were given a positive rating. There was no remarkable difference between the two o/w creams themselves.

In contrast, differences between the placebo and the formulation containing the active substances could be seen in all three expedient systems. This effect was most pronounced in the "shaking emulsion" expedient system, which was also confirmed by all subjects from a subjective point of view.

Comparative Example 2

After the above mentioned results had been obtained, experiments were performed for the "shaking emulsion" expedient system with analogous compositions, but comparing the primary tinctures from *Phyllanthus emblica* with a 50% to 50% mixture of *Centella asiatica* and *Bacopa monnieri*. The primary tinctures from both medicinal plants were incorporated in the above shaking emulsion base in a concentration of 5% by weight each, and the amount of the oil phase was correspondingly reduced.

The effectiveness of the two formulations was compared, again in a half-sided application test in a group of 10 subjects. The subjects were predominantly females aged between 45 and 60 years. The duration of the experiment was six weeks.

The products were applied to one half of the face in the morning and in the evening after cleaning the face as usual. In addition to the usual evaluation of smoothness and elasticity of the skin as well as the subjective feeling by the subjects, such as skin tension, feeling of dryness and the like, two further parameters were used. A significant sign of epidermic proliferation (regeneration of the skin cells) is the shedding of the dead cells of the horny layer. Since the regenerated skin layer is characterized by smoothness and a fresh complexion, the depth of the wrinkles in the eye, mouth and forehead areas was included in the evaluation. The evaluation rate was increased from twice to three times a week.

In 60% of the subjects, a clear scaling of the horny layer was detected after three weeks of application. After another week of application, the same was observed with the remaining 40% of the subjects, who were over 55 years old. After six weeks, at the end of the application test, the wrinkles in the face had almost disappeared in all subjects, and even the deeper wrinkles had clearly shallowed. Thus, proof of epidermic proliferation could be furnished.

Between the two primary tinctures from *Phyllanthus emblica* and *Centella asiatica* and *Bacopa monnieri*, gradual differences could be observed in favor of the first. It was found that the half of the face treated with shaking emulsions containing amla tincture had a smoother and fresher appearance, and regeneration of the skin could be detected some days earlier. From the components of the amla tincture (mucic acids, tannins, fruit sugars, free amino acids, vitamin C and others), as described above, this result would have been expected.

In addition to the normalization or promotion of natural regeneration (proliferation of cells) of old, mature skin, the shaking emulsion according to the invention is also especially suitable for the treatment of common acne, puberty acne and other skin impurities, such as comedones and the like. Its activity is presumably attributable to two factors:

Due to their different spreading effects, the natural triglycerides (oils) penetrate to different depths of the skin layers and thus also reach the sebaceous glands. They dissolve the sebum and thus enable it to flow freely to the surface of the skin. Thus, obstruction of the sebaceous glands and ducts is prevented.

The medicinal plant extracts and vitamins are also carried to deeper skin layers by the natural oils. They cause normalization of the cell activities and have an antiphlogistic effect.

It could be established that the purposeful addition of

| | |
|---|---|
| *Aloe barbadensis* (10 fold concentrate) | 3 to 5% by weight |
| *Hibiscus sabdariffa* (flower extract) | 2 to 6% by weight |
| algal gel | 3 to 6% by weight | to the shaking emulsion as well as to the o/w and w/o emulsions substantially improves the care-providing properties (such as smoothness, softness, moisturizing effect) of these products.

Example 1

After an interruption of the experiment of several months, another experiment was run on the same subjects to detect the synergistic effect of a combination of *Phyllanthus emblica* and a 50% to 50% mixture of *Centella asiatica* and *Bacopa monnieri*. To this end, the primary tinctures from *Phyllanthus emblica* and a 50% to 50% mixture of *Centella asiatica* and *Bacopa monnieri* were incorporated in the above shaking emulsion base in a concentration of only 2% by weight each.

All other experimental conditions and the evaluation parameters were left unchanged.

Surprisingly, it was found that a clear scaling of the horny layer had occurred in about 75% of the subjects after two weeks of application already. The same experience had the remaining 25% of the subjects after 3 weeks, so that the additional application of a commercially available face peeling cream was recommended to remove the dead skin cells of the horny layer. The different ages of the subjects played no essential role in this case.

This result shows the synergistic effect of the primary tinctures from *Phyllanthus emblica* and a 50% to 50% mixture of *Centella asiatica* and *Bacopa monnieri*, because a better epidermic proliferation could be achieved in less time and at a lower concentration than with the individual tinctures. The result after only 3 weeks of application of the above described shaking emulsion was a smooth, elastic and fresh appearing skin with clearly reduced wrinkles in the face, which could be objectively percepted. Even when the application was reduced to once a day over night, the skin could be maintained in an attractive and healthy appearing condition for extended periods of time. Since this application test was performed over nearly two years, variations due to the change of seasons could be excluded.

Example 2

In the further course of the studies, a combination of active ingredients of primary tinctures from *Phyllanthus emblica* and a 50% to 50% mixture of *Centella asiatica* and *Bacopa monnieri* was also added to the o/w cream formulations on the basis of non-ionogenic emulsifiers in amounts of 2% by weight of amla and 3% by weight of the 50% to 50% mixture of *Centella asiatica* and *Bacopa monnieri,* and the skin-regenerating properties of the formulations were tested. A comparable result could be achieved with these formulations as well.

Example 3

Cosmetic Formulation for Non-genetically Caused Loss of Hair and Hair Care Product In practical application, it could be proven that the use of *Phyllanthus emblica* and *Centella asiatica* and/or *Bacopa monnieri* in suitable concentrations and expedient systems results in a normalization of the proliferation of cells (regeneration of the skin) with older and mature skin.

Surprisingly, when the inventive combination of active substances according to Example 2 is applied, the activity of the scalp cells was also normalized or stimulated by the use of *Phyllanthus emblica, Bacopa monnieri* and *Centella asiatica* as well as additional medicinal plants. A great number of medicinal plant extracts were tested. The following plant extracts had a stimulating effect and were processed into a complex of active ingredients:

Complex of Active Ingredients for Loss of Hair and Stimulation of Hair Growth

| | |
|---|---|
| *Phyllanthus emblica* | 25 parts |
| *Bacopa monnieri* | 10 parts |
| *Centella asiatica* | 10 parts |
| *Abies balsamaea* (silver fir cone oil) | 20 parts |
| *Mentha arvensis, piperascens* (oil) | 10 parts |
| *Hibiscus sabdariffa* (flower extract) | 10 parts |
| *Melia azadirachta* (leaf extract) | 5 parts |
| *Citrus bergamia* (bergamot oil) | 5 parts |
| *Citrus aurantifolia* (lime flower oil) | 5 parts |
| total: | 100 parts |

Based on this combination of active ingredients, the following cosmetic formulations for non-genetically caused loss of hair and for the promotion of normal hair growth were prepared:

Medicinal hair tonic

| | | preferred formulation |
|---|---|---|
| combination of active ingredients according to Example 1 | 1–50% | 15% |
| care substances and vitamins (1-menthol, D-panthenol, camphor, β-estradiol, nicotinamide) | 0.5–3.0% | 1.5% |
| adjuvants PEG-40 hydrogenated castor oil solvent ethoxydiglycol | 0.3–1.5% | 0.5% |
| perfume oil | 0.3–1.0% | 0.5% |
| isopropanol | 20.0% | 20.0% |
| ethanol | ad 100% | 62.5% |
| total: | | 100% |

Hair treatment (emulsion form)

| | | preferred formulation |
|---|---|---|
| cetylstearyl alcohol | 0.5–2.0% | 0.5% |
| non-ionogenic emulsifier | 2.5–5.0% | 3.5% |
| oil components (as with shaking emulsion + *Melia azadirachta* kernel oil) | 3.0–25.0% | 20.0% |
| combination of active ingredients according to Example 1 | 2.0–30% | 20.0% |
| glycerol 86% | 1–5% | 3.0% |
| citric acid | 0.1–0.5% | 0.5% |
| dem. water | ad 100% | 52.5% |
| total: | | 100% |

Experimental Example:

In the preceding experiments (duration about 3 months), the products were applied as follows:

hair treatment: twice a week duration of action, at least: 30 minutes preferably: 60 minutes hair tonic: daily in the morning and in the evening, but at least once daily and always after washing the hair.

The hair tonic was not washed off and remained on the head. It was gently massaged into the scalp with circling movements of the fingertips.

Result:

After about 10 weeks of application, a significant reduction of the hair loss could be detected.

The growth of the existing hair was also significantly promoted.

To promote the treatment of the scalp and to reduce loss of hair, three mild shampoo formulations were developed, namely for:

normal and fine hair greasy and dandruffy hair dry hair.

A shampoo formulation for normal and fine hair is exemplified as follows:

| | |
|---|---|
| mixture of mild detergent surfactants | 40% |
| care substances and fabric softeners (natural triglycerides, e.g., oil of sweet almonds or apricot kernel oil, guar hydroxypropyltri-ammonium, chloride and refatting agent) | (0.5–2%) preferably 1.0% |
| combination of active ingredients according to Example 1 | (1–8%) preferably 3.0% |
| solution of preservatives | 1.0% |
| perfume oil | 0.2% |
| demin. water | 54.8% |
| total: | 100% |

What is claimed is:

1. A cosmetic formulation for topical application comprising:

(a) an extract from *Phillanthus emblica;*

(b) an extract from *Centella asiatica* or an extract from *Bacopa monnieri;* and (c) a pharmaceutically acceptable carrier.

2. The formulation of claim 1 wherein the extract from *Phyllanthus emblica* is an extract from fresh fruit, dried fruit, or both.

3. The formulation of claim 1 wherein the extract from *Centella asiatica* or the extract from *Bacopa monnieri* is obtained from stalks, flowers, leaves, roots, or combinations thereof of plants.

4. The formulation of claim 1 comprising 1 to 20% by weight of the extract from *Phyllanthus emblica,* and 1 to 20% by weight of the extract from *Centella asiatica* or the extract from *Bacopa monnieri.*

5. The formulation of claim 1 wherein the pharmaceutically acceptable carrier is selected from the group consisting of vegetable oils, alcohols, emulsifiers, antioxidants, thickeners, UV absorbers, vitamins, minerals, trace elements, perfumes, and or mixtures thereof.

6. The formulation of claim 1 further comprising extracts from *Aloe barbadensis* and *Hibiscus sabdariffs.*

7. A method of accelerating epidermic proliferation comprising applying to human skin an effective amount of the formulation of claim 1.

* * * * *

UNITED STATES PATENT AND TRADEMARK OFFICE
CERTIFICATE OF CORRECTION

PATENT NO. : 6,361,804 B2 Page 1 of 1
DATED : March 26, 2002
INVENTOR(S) : Shyam B. Singh-Verma It is certified that error appears in the above-identified patent and that said Letters Patent is hereby corrected as shown below:

Column 8,
Line 59, "*Phillanthus*" has been replaced with -- *Phyllanthus* --.

Signed and Sealed this

Eleventh Day of February, 2003

JAMES E. ROGAN
*Director of the United States Patent and Trademark Office*